United States Patent [19]

Inouye et al.

[11] 4,189,775
[45] Feb. 19, 1980

[54] METHOD AND APPARATUS FOR SUBSECTION ANALYSIS USING COMPUTED TOMOGRAPHY

[75] Inventors: Tamon Inouye, Tokyo; Hiroyuki Mizutani, Kawasaki; Toshio Uehara, Tokyo, all of Japan

[73] Assignee: Tokyo Shibaura Electric Co., Ltd., Japan

[21] Appl. No.: 874,064

[22] Filed: Jan. 31, 1978

[30] Foreign Application Priority Data

Jan. 31, 1977 [JP] Japan .................................. 52-8702
Jan. 31, 1977 [JP] Japan .................................. 52-8704

[51] Int. Cl.² ............................................. G01T 1/16
[52] U.S. Cl. .................. 364/414; 250/445 T; 358/160; 364/515; 364/572
[58] Field of Search ................ 364/414, 515, 572; 250/363 S, 445 T; 358/160, 167, 168

[56] References Cited

U.S. PATENT DOCUMENTS

| 3,752,982 | 8/1973 | Jaszczak | 250/445 T |
| 3,778,614 | 12/1973 | Hounsfield | 250/363 S |
| 3,924,129 | 12/1975 | Lemay | 250/445 T |
| 4,030,119 | 6/1977 | Ellis | 358/160 |
| 4,042,811 | 8/1977 | Brunnett et al. | 250/445 T |
| 4,066,903 | 1/1978 | Lemay | 250/445 T |
| 4,115,805 | 9/1978 | Morton | 364/515 |

OTHER PUBLICATIONS

Stark, "An Optical-Digital Computer for Parallel Processing of Images", IEEE Trans. on Computers, vol. C-24, No. 4, Apr. 1975.

Primary Examiner—Errol A. Krass
Attorney, Agent, or Firm—Finnegan, Henderson, Farabow & Garrett

[57] ABSTRACT

An apparatus and method for tomographic analysis comprising a detecting system for detecting a number of radiation beams having penetrated a sectional area of a subject and producing projection data signals; a CPU and a memory for applying a filter function to the projection data signals by a convolution integration or by a computational technique included in a filtered-back projection, thereby calculating modified projection data signals, and conducting back projection operations only with respect to points in a partial region or subsection of the sectional portion area by means of the modified projection data, thereby calculating the radiation beam absorption coefficients at said points, the integral operation used in the calculation of the modified projection data signals being limited to an interval in which the quality of an image of said partial region or subsection to be displayed can exclusively be improved by the filter function; and a display unit for displaying the image of the partial region on the basis of said absorption coefficients.

6 Claims, 9 Drawing Figures

METHOD AND APPARATUS FOR SUBSECTION ANALYSIS USING COMPUTED TOMOGRAPHY

BACKGROUND OF THE INVENTION

This invention relates to an apparatus for performing computed tomography comprising a radiation source for projecting a number of radiation beams in various directions from the outer periphery of a sectional portion of a subject to be displayed in parallel with both sides of the sectional portion, a detecting system for detecting radiation beams having penetrated the sectional portion and producing projection data signals corresponding to the strength of the respective radiation beams, a projection data memory for storing the signals in sets each corresponding to a fixed number of beams parallel to a predetermined direction of projection, and a display unit for displaying an image in accordance with the distribution of the radiation absorption coefficients at multitudinous points of the sectional portion, as well as to a method for effecting tomographic analysis by using the above mentioned apparatus.

This general type of apparatus is already known. According to the principle of such apparatus, data produced by projection of the radiation absorption coefficients at various parts of the transmission path, i.e. projection data, are obtained from radiation beams penetrating the sectional portion of the subject in parallel therewith and in fixed directions of projection at varied angles, and then the projection data are filtered for the calculation of modified projection data. A modified reconstructed image is obtained by conducting back projection on the basis of these modified projection data, and is displayed on the display unit. The filtering operation is performed in order to remove fuzziness or blurring that may be caused if the image is constructed from the data back projected as they are. Already known are a number of methods in which an image is reconstructed from modified projection data. The methods of convolution integration and filtered-back projection among others are known as acceptable methods for image reconstruction. Being well-known, these methods are excluded from the description herein. With conventional reconstruction methods, the integral computation employed for the convolution operation, Fourier transform, inverse Fourier transform, and the aforesaid back projection is based on an integral interval covering the whole area of a plane that crosses the subject, and reconstruction of the image of the sectional portion of interest is done only by conducting these operations.

In displaying the interior of the subject, e.g. in diagnosing the interior of the body of a patient, however, the sectional portion hardly requires overall display, often requiring only partial display, that is, of a specified or partial region to be observed. Nevertheless, in the prior art methods, reconstruction of the image would be performed also for unnecessary portions, requiring much time for operation. Convention systems, in which image reconstruction is conducted by the aforesaid operations, have been considered incapable of reconstructing and displaying an image of a partial region.

An object of this invention is to provide a method and apparatus for tomographic analysis by means of penetrating radiation capable of reconstructing an image of a specified region or partial region in a sectional portion of a subject in a short time without substantially deteriorating its quality as well as of displaying such image by utilizing part of the projection data relating to the sectional portion.

SUMMARY OF THE INVENTION

In order to attain the above object, the apparatus of the invention is provided with a modified data calculating system for applying to projection data a filter function for the removal of fuzz distortion or blurriness that may be caused in a displayed image of a specified region of the sectional portion under examination, the projection data signals being included in sets of projection data signals, thereby forming sets of modified projection data. The system further applies an integral interval for integral operation used in the modified data calculating system consisting of a section corresponding to the specified region and an additional region added thereto, the additional region being so defined as to allow the integral operation within the additional region to affect the quality of the image of the specified region displayed on the basis of the modified projection data but not to allow further integral operation beyond the additional region to affect the image quality. Further, the apparatus includes a back projection system for conducting the integral operation for back projection only with respect to a number of points included in the specified region in each corresponding direction by means of the sets of modified projection data signals, thereby calculating the absorption coefficients at such points and supplying the coefficients to a display unit. The method according to the invention further includes processes in which the modified data calculating system and back projection system are employed for reconstructing and displaying an image of the sectional portion.

According to the apparatus and method of this invention, the integral operation for obtaining the modified projection data is conducted only with respect to a section corresponding to the specified or partial region, plus an additional region that is minimally large enough to apply the filtering effect substantially completely to such region, and the integral operation for the back projection is limited to points within the partial region. Notwithstanding the limited integration interval, no deterioration of the quality of the image display is realized, and the time required to generate the display is substantially reduced.

BRIEF DESCRIPTION OF THE DRAWINGS

This invention can be more fully understood from the following detailed description when taken in conjunction with the accompanying drawings, in which.

DETAILED DESCRIPTION OF EMBODIMENTS

In a first embodiment of the apparatus of this invention a convolution integration is employed for obtaining modified projection data from the basic projection data, while in a second embodiment a novel computation technique is employed in a filtered-back projection method for the same purpose.

Figure 1:
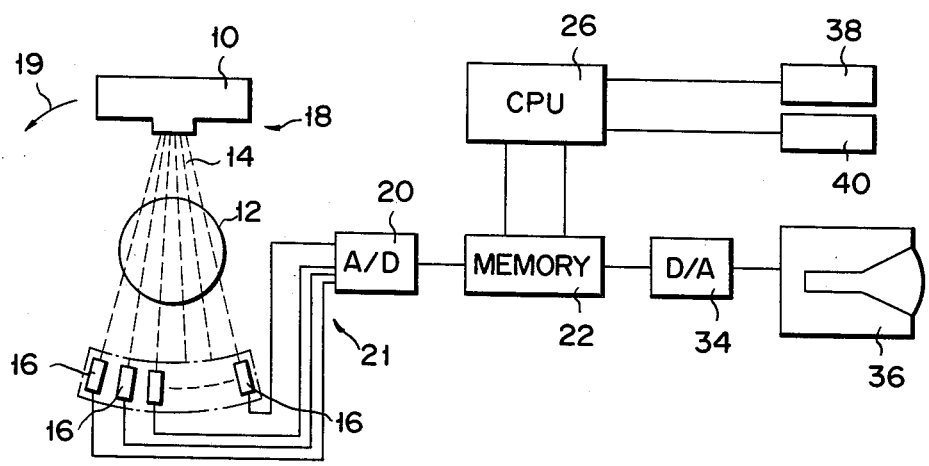
FIG. 1 is a block diagram illustrating the general configuration of the apparatus of this invention.

Looking at FIG. 1, a radiation source 10 produces a number of radiation beams 14 spreading out fanwise, which are projected through a thin sectional portion or area 12 of a subject, and detected by detectors 16 after penetrating the sectional portion 12. The radiation source 10 and detectors 16 are driven by a scanner 18 (not shown) to revolve in the direction indicated by arrow 19, thereby projecting a set of beams 14 at various fixed angles and inducing such beams 14 to penetrate the sectional portion 12. Being of well-known construction, the scanner 18 will not be described in detail herein.

A detector 16 is provided for each of the beams 14. Each detector is arranged to detect a beam and generate an electric signal indicating the strength of the transmitted beam. The detectors 16, along with an A/D converter 20, form a detecting system 21, the A/D converter 20 producing projection data signals which represent the projections of the radiation absorption coefficients at various parts of the transmission paths of the beams 14. These projection data are stored in a memory 22.

Figure 2:
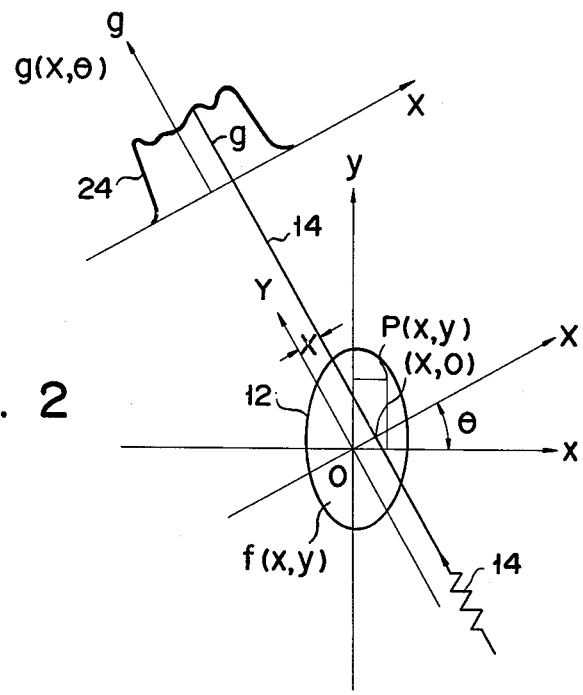
FIG. 2 is a schematic diagram showing the relation between a sectional portion of a subject, the coordinate systems providing the basis for operation, and the directions of projection of radiation beams.

Referring now to FIG. 2, there will be described the projection data. In FIG. 2 the sectional area 12 is disposed in parallel with the plane of the paper, on which there are arranged two rectangular coordinate systems (x, y) and (X, Y) rotationally displaced from each other by an angle $\theta$ about a suitably selected point of origin O. The coordinate system (x, y) is fixed on the sectional area 12, while the coordinate system (X, Y), accompanies the rotation of the radiation source 10, and therefore revolves by the same angle as that of the rotation of the beams 14.

A radiation beam 14 is emitted from the radiation source 10 (FIG. 1), passes through a point (X, O) in the coordinate system (X, Y), penetrating the sectional portion 12 along a path parallel to the Y-axis, and is received by its corresponding detector 16 (not shown) disposed in the beam path. A rectangular coordinate system (X, g) arranged at the position end of the Y-axis of FIG. 2 is a coordinate system in which the normal distance of the beam path away from the Y-axis lies along the abscissa and the value of the projection data "g" produced by the detecting system 21 is plotted along the ordinate, while the length of the plotted bar or line "g" shows the projection data produced by the beam 14.

As shown in FIG. 1, the radiation source 10 emits beams 14 spreading out fanwise at different angles $\theta$ while rotating about the sectional portion 12, so that there are obtained a number of projection data from a number of beams penetrating the sectional portion 12 at different angles. In FIG. 2 "g" represents a projection data value from a beam 14 having penetrated the sectional portion while intersecting the X-axis at a point (X, O) among a number of beams admitted during the rotational scan so as to pass through the area 12 in a direction parallel to the Y-axis which is defined by the angle $\theta$. Since the values of "g" will change with X and $\theta$, it will be referred to as the function $g(X, \theta)$ in the case where it is more convenient to specify the relation in terms of X and $\theta$.

Among the aforesaid number of beams those which are projected in parallel with the illustrated beam intersect the X-axis at varied points. In the coordinate system (X, g) of FIG. 2, the different values of $g(X, \theta)$ represented therein are not individually shown for the sake of simplicity but there is drawn the envelope of these $g(X, \theta)$ values, that is, the projection profile 24. Values $g(X, \theta)$ involving various X points at a given $\theta$ will hereinafter be collectively referred to as a set of projection data regarding the angle $\theta$. These values $g(X, \theta)$ represent sampling data corresponding to the projection profile 24. Theoretically, the projection data should be measured at infinitely close intervals to provide the above continuous projection profile 24. Such measurements are not, however, practical because the measurement, as well as the processing operations thereafter, becomes too complex and time consuming. Therefore, the projection data are obtained by sampling the projection data outputs at a limited but reasonable frequency, and the image of the sectional portion is reconstructed and displayed in accordance with these data outputs.

Returning now to FIG. 1, the memory 22 comprises a program memory for storing the program of a computer or CPU 26 for classifying the projection data from a number of beams corresponding to the various angles $\theta$ of FIG. 2 according to the fixed directions of projection, and hence the various angles $\theta$. The memory 22 further includes a section for storing the projection data, an h(X) data memory section for storing a filter function h(X), as described below, and a reconstructed-image memory section. The data computer 26 performs operations required for filtering and reconstructing an image based on the projection data, and for storing the results in the reconstructed-image memory section.

Figure 3:
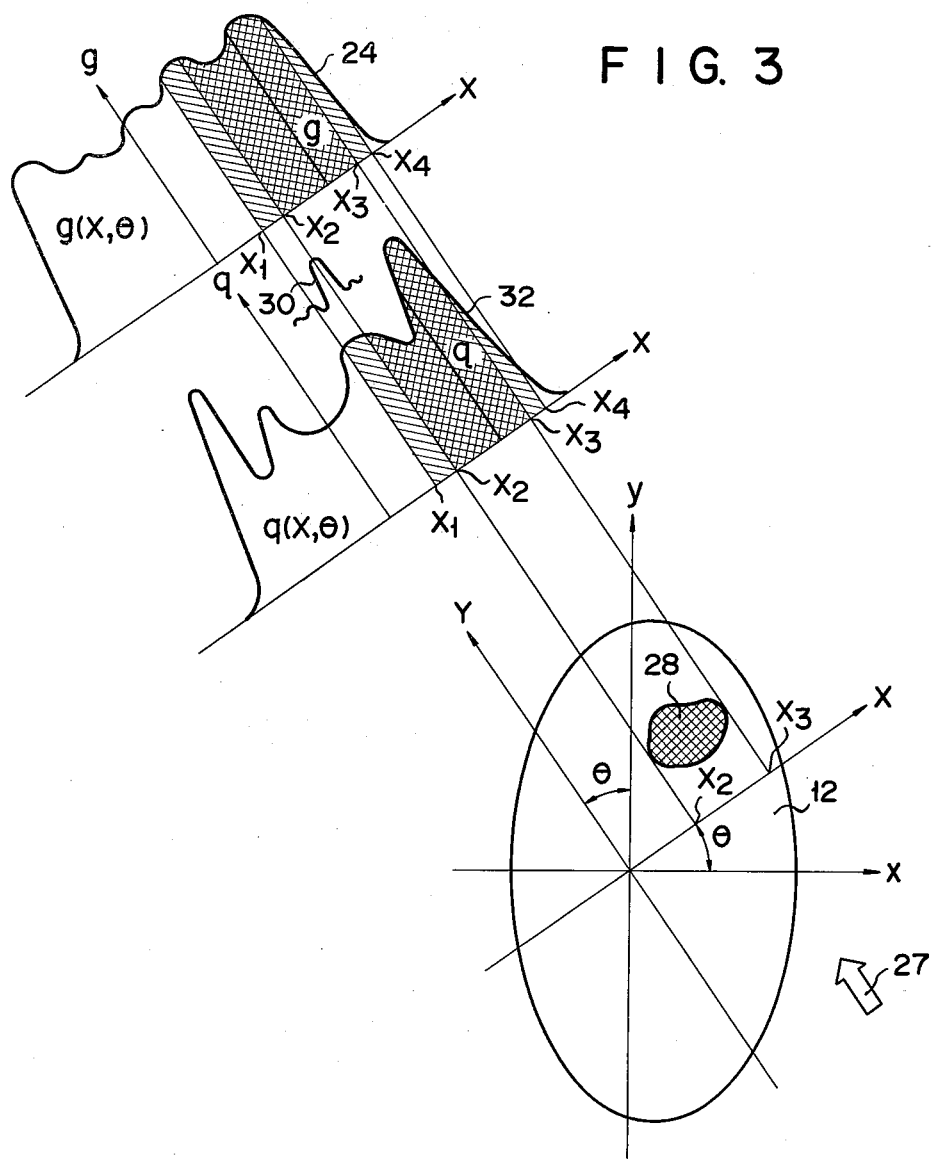
FIG. 3 is a schematic diagram illustrating a sectional portion with a specified partial region and integral intervals defined in accordance with the invention for calculating modified projection data.

Now there will be described the principle of the filtering operation employed in the present embodiment. In FIG. 3, just as in FIG. 2, there are shown the sectional portion 12 of the subject under examination and the projection profile 24 obtained from a number of substantially beams as indicated collectively by an arrow 27. Numeral 28 denotes a partial region or subsection within in the sectional area 12 which and is specified for display. Numeral 23 designates a profile of modified projection data values $q(X, \theta)$ (found by way of sampling) obtained by subjecting each projection data value $g(X, \theta)$ to the filtering operation described below. These data are indicated by g and q in FIG. 3. In the profiles 24 and 32 the range from $X_2$ to $X_3$ on the X-coordinate corresponds to the projection of the partial region 28.

In this embodiment the operations for calculating a modified projection data value q(X, θ) from each projection data value g(X, θ) includes:

$$q(X,\theta) = \frac{1}{2} \int_{X_\alpha}^{X_\beta} g(X',\theta)h(X - X')dX'. \quad (1)$$

Where $$h(X) = \frac{1}{2\pi} \int_{-\infty}^{\infty} H(\omega)e^{i\omega X}d\omega, \quad (2)$$

and h(X) is a filter function for real space, H(ω) is a Fourier transform of h(X), "ω" is a frequency introduced in th Fourier transform, X' is a variable introduced in the convolution integration given by equation (1). Equations (1) and (2) are further described as follows.

The starting point of equation (1) is the following equation (3) regarding the well-known filtering operation.

$$q(X,\theta) = \frac{1}{4\pi} \int_{-\infty}^{\infty} [\int_{-\infty}^{\infty} g(X,\theta)e^{-i\omega X}dX] \cdot |\omega|e^{i\omega X}d\omega \quad (3)$$

Here ω is the frequency described with reference to equation (2), |ω| is a filter function for the frequency domain, and "i" is an imaginary unit. As is understood from the expression of equation (3), the integration in equation (3) involves entire sectional portion 12 of the subject and is conducted for the whole area irradiated with radiation beams.

Figure 4:
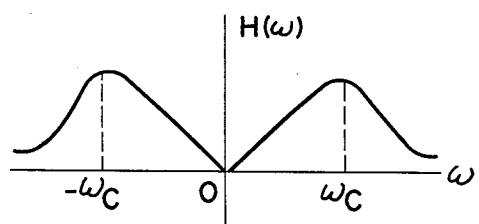
FIG. 4 is a graph showing a curve of a filter function in the frequency domain.

In the above equation |ω| increasingly diverges as the absolute value of ω increases. Since the filter function |ω| cannot be used in its known form for the purposes of the invention, there is used instead thereof a function H(ω) which approaches asymptotically to 0 outside a fixed range of ω as shown in FIG. 4.

In accordance with the above considerations, equation (3) may be rewritten as follows:

$$q(X,\theta) = \frac{1}{4\pi} \int_{-\infty}^{\infty} [\int_{-\infty}^{\infty} g(X,\theta)e^{-i\omega X}dX]H(\omega)e^{i\omega X}d\omega \quad (4)$$

Then, employing the well-known theorem for Fourier transformation, equation (4) is further transformed for simplicity of integration. This theorem goes as follows: "Application of a filter function to the Fourier transform of a certain function in the frequency region, i.e. multiplying of the Fourier transform by the filter function, is equivalent to convolution of the inverse Fourier transforms of both the certain function and the filter function in the real space." According to this theorem, equation (2) may be rewritten as follows:

$$q(X,\theta) = \frac{1}{2} \int_{-\infty}^{\infty} g(X',\theta)h(X - X')dX' \quad (5)$$

where h(X) and X' are the same as in equations (1) and (2).

Figure 5:
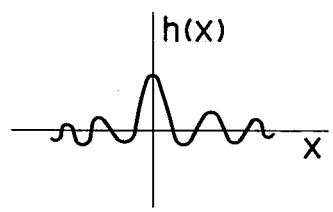
FIG. 5 is a graph showing a curve of the filter function of FIG. 4 in real space.
Figure 6:
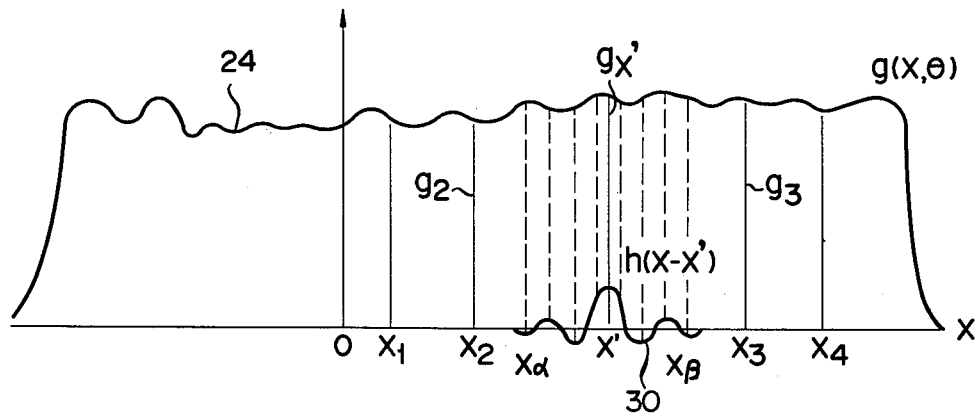
FIG. 6 is a graph showing the relationship between the projection data, the filter function in real space, and various integral intervals.

FIGS. 4 and 5 show graphs of H(ω) and h(X) respectively. A curve 30 shown in FIG. 3 describes the filter function h(X). FIG. 6 shows enlarged views of the projection profile 24 and filter function 30 i.e. h(X) shown in FIG. 3. In FIG. 6 the filter function h(X) is shifted to a point X' on the X-axis and expressed in the form of h(X-X') as designated by numeral 30. The aforesaid integral expression (5) indicates that half of the integral of the product of g(X', θ) at position X' and the filter function h(X-X') as obtained with respect to X' is equal to q(X, θ).

Further, considering equation (5), we see h(X) converges to 0 as the absolute value of X increases, so that the value of g(X', θ)h(X-X') converges to 0 as X is displaced further from X'. Accordingly, the integration interval of equation (5) may be properly reduced from $-\infty \sim \infty$ to $X_\alpha \sim X_\beta$. This interval is determined by the spread of the filtering function, i.e., it is so defined that the varying of the integration interval within the interval $X_\alpha \sim X_\beta$, i.e., reducing it to a narrower interval, may change the quality of the displayed image of the partial region, but the varying of the interval beyond the interval $X_\alpha \sim X_\beta$ i.e., expanding it to a wider interval does not change the quality, that is, does not affect the density of the displayed image of the partial region. Therefore, in this embodiment the actual operation is conducted with the integral interval reduced to $X_\alpha$ to $X_\beta$. This reduced integral interval corresponds to that employed in equation (1).

The above description will be further supplemented with reference to FIG. 6. FIG. 6 illustrates a case in which a projection data value g(X') is modified by the filter function h(X). The filter function h(X) is shifted by X' in the direction of the X-axis. As mentioned above, h(X-X') converges to 0 at both right and left ends of the graph.

As already mentioned, $X_2$ to $X_3$ is a range of beams which have penetrated the partial region 28 in the sectional portion designated for display. Modification of the projection data g(X, θ) should be made only for the beams included within the range $X_2$ to $X_3$. In order to modify substantially completely the projection data $g_2$ at one end $X_2$ of such range $X_2$ to $X_3$, however, integration should be conducted as far as the position of $X_\alpha$, i.e. position $Y_1$, where the center of the filter function h(X) is superimposed on $X_2$. Likewise, in order to modify satisfactorily the projection data value $g_3$ at the other end $X_3$ of the range $X_2$ to $X_3$, integration should be conducted out to the maximum position of $X_\beta$, i.e. $X_4$. The positions of $X_1$ and $X_4$ in FIGS. 3 and 6 are points representing $X_\alpha$ and $X_\beta$.

Repeating the above operation, we may obtain a plurality of sets of modified projection data values q(X, θ) regarding the beams included in basic projection profile 24 and passing through various points on the X-axis. Numeral 32 (FIG. 3) designates an envelope or profile of these data values q(X, θ). The q(K, θ) should be obtained only with respect to X values within the range $X_2$ to $X_3$. After the reduced profile 32 is obtained with respect to a certain angle θ (FIG. 3), additional reduced profiles are successively obtained for various different values of θ. Thus obtained, the modified projection data are stored in the memory 22 of FIG. 1.

The central processing unit or CPU 26 as shown in FIG. 1 reads out the modified projection data q(X, θ) calculated by the above filtering operation from the memory 22, and performs the operation for reconstruction of the desired image in accordance with $$f(x,y) = \frac{1}{2\pi} \int_0^{2\pi} q(X,\theta)d\theta \quad (6)$$

-continued
$$= \frac{1}{2\pi} \int_0^{2\pi} q(x \cdot \cos\theta + y \cdot \sin\theta, \theta)d\theta$$

where $$X = x \cdot \cos\theta + y \cdot \sin\theta$$

According to equation (6), there is obtained a radiation absorption coefficient f(x, y) at a point (x, y) in the partial region or subsection 28 (FIG. 3). By conducting such operation for various points in the partial region, the absorption coefficients at various parts of such subsection may be obtained, and thus a two-dimentional variable-density image of the selected region is reconstructed. The reconstructed-image data calculated according to equation (6) is stored in the reconstructed-image memory section in the aforesaid memory 22, read out as occasion demands, converted into an analog signal by a DA converter 34, and displayed by display units 36 and 38 (FIG. 1). The display includes printing-out the image data by a printer 38 as well as display by a cathode ray tube (CRT) 36 or the like. An input unit 40 is used for supplying the computer 26 with various external commands and instructions designating the specified region 28 in the subject to be displayed, for example.

Figure 8:
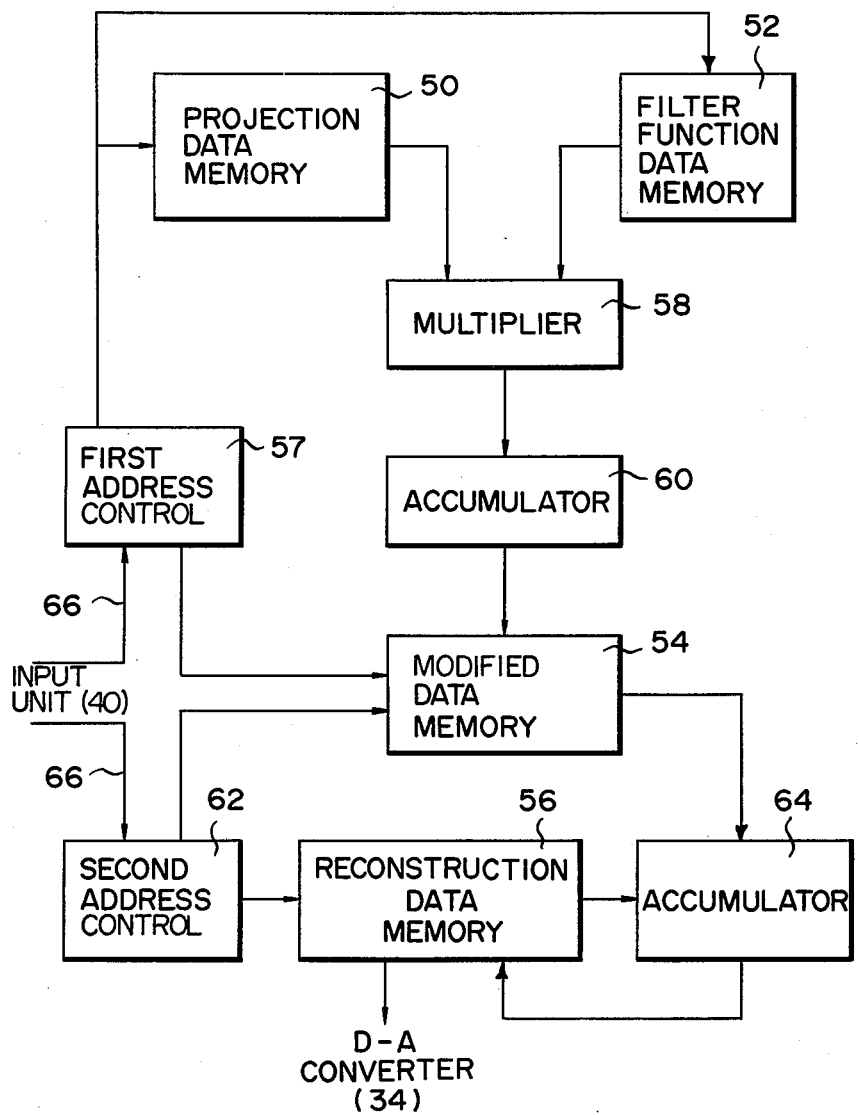
FIG. 8 is a block diagram showing a modified data calculating system and a back projection system where convolution integration is employed for calculating the modified projection data.

FIG. 8 is a block diagram showing a system, using the above-described convolution integration method for image reconstruction processing in accordance with the invention. A projection data memory 50 stores as sampling data a number of projection data values g(X, θ) included in sets collected for predetermined angles θ. Likewise, a filter function data memory 52 stores the sampling data values for the filter function h(X). A modified data memory 54 stores sets of modified projection data q(X, θ) separately corresponding to the sets of projection data, while a reconstruction data memory 56 stores data representing the absorption coefficients at various points in the selected partial region or subsection obtained by back projection calculation. These memories are included in the memory unit 22 of FIG. 1.

A first address control circuit 57 designates the addresses of the projection data memory 50 and filter function data memory 52, reads out the data of the respectively designated memory addresses by means of a readout circuit (not shown), and supplies the data to a multiplier 58. This multiplier 58 multiplies these two data by each other and delivers the product to an accumulator 60, where the calculation results of the multiplier 58 are accumulated for every θ value as indicated by the projection data g(X, θ), and supplied to the modified projection data memory 54. This memory 54 stores the calculation results of the accumulator 60 in an address designated by the first address control 57. These operations are performed successively for the projection data values g(X, θ) corresponding to every angle θ. Thus, the first address control 57, projection data memory 50, filter function data memory 52, multiplier 58, accumulator 60, and modified data memory 54 form a modified data calculating system to carry out the convolution integration procedure defined by equation (1).

Meanwhile, a second address control circuit 62 successively designates the addresses of the modified data memory 54, reads out data with respect to the desired X location from sets of a number of modified projection data values corresponding to specified angles θ, and supplies the data to a second accumulator 64. The accumulation results produced by the accumulator 64 are stored in the address designated by the second address control 62 of the reconstruction data memory 56. Such operation is repeated for all small portion, e.g., pixels of the partial region 28. The second address control 62, modified data memory 54, second accumulator 64, and reconstruction data memory 56 form a back projection system to carry out the computations defined by equation (6).

The operations performed by the control circuits of FIG. 8, that is, first address control 57, multiplier 58, accumulator 60, second address control 62, and accumulator 64 may be performed solely by the computer 26 of FIG. 1 under appropriate program control. When the partial region or subsection 28 (FIG. 3) of the sectional portion is designated by the input unit 40, a designating signal 66 is supplied to the first and second address controls circuits 57 and 62 of FIG. 8. When supplied with the partial region designating signal 66, the first address control 57 conducts address designation so as to read out the data from the projection data memory 50 and filter function data memory 52 only with respect to the ranges $X_1$ to $X_4$ illustrated, for example, in FIG. 3.

Receiving the partial region designating signal 66, the second address control 62 conducts address designation so as to read out the data from the modified data memory 54 only with respect to the range corresponding to the partial region 28 of FIG. 3, i.e. $X_2$ to $X_3$. The operation for back projection, in this case, is performed by accumulating the modified projection data values q(X, θ) at specified angles θ with respect to a specified value of X(= x·cos θ + y·sin θ), the accumulation being conducted for various points (x, y) within the range of the partial region 28.

According to this invention, as described above, the operations should be performed only for the designated partial region by using as the starting materials data the projection data values obtained from beams penetrating a somewhat wider range corresponding to said region, so that the time required for the image-reconstruction operation may be substantially reduced. Although in this case the data available for the reconstruction may be limited to a small number of samples obtained within a narrow range, no deterioration of the quality of the displayed image will occur.

Various modifications of the above-described embodiment may be devised. For example, either parallel beams or fan beams may be used for the means to penetrate the subject in a number of different directions. Further, there may be employed methods in which the subject is irradiated externally by either rotary or parallel motion of the beam projection mechanism, or by a combination of rotary and translational motion. Additionally, the subject may be irradiated from an internal source such as an injected radioisotope solution.

It is to be further understood that a dedicated-function control device may be employed for the arithmetic unit instead of the general purpose computer described above.

Now there will be described a second embodiment of the invention in which a computation method employed in the filtered-back projection operation is used for calculating the modified projection data. Since the drawings of FIG. 2 and 3 and the description presented above for the first embodiment are applicable also to this embodiment, the description of the coordinate systems, projection data, modified projection data, and projection profile are not repeated herein. Further, FIG. 1 illustrating the overall configuration of the apparatus and FIG. 4 showing the filter function H(ω) as given in the frequency domain also apply for the second embodiment.

In this embodiment the modified projection data values q(X, θ) are calculated from each data value g(X, θ) according to $$q(X,\theta) = \frac{1}{4\pi} \int_{-\infty}^{\infty} G'(\omega,\theta)H(\omega)e^{i\omega X}d\omega \quad (7)$$

The derivation of equation (7) is as follows. In general, equation (1) is employed for obtaining the modified data values q(X, θ) from the projection data values g(X, θ), while equation (1) is rewritten into equation (4) by substituting H(ω) for |ω| in the same manner previously described for the first embodiment.

Then, equation (4) is rewritten as follows:

$$q(X,\theta) = \frac{1}{4\pi} \int_{-\infty}^{\infty} G(\omega,\theta)H(\omega)e^{i\omega X}d\omega \quad (8)$$

where $$G(\omega,\theta) = \int_{-\infty}^{\infty} g(X,\theta)e^{-i\omega X}dX \quad (9)$$

Here G(ω, θ) is the Fourier transform of g(X, θ).

According to the fundamental principles of the filtered-back projection method, the projection data g(X, θ) is transformed to the frequency domain by Fourier transformation multiplied by the filter function H(ω), transformation by inverse Fourier transform to calculate the modified projection data, the back-projected for reconstruction and display of an image of the sectional portion.

Figure 7:
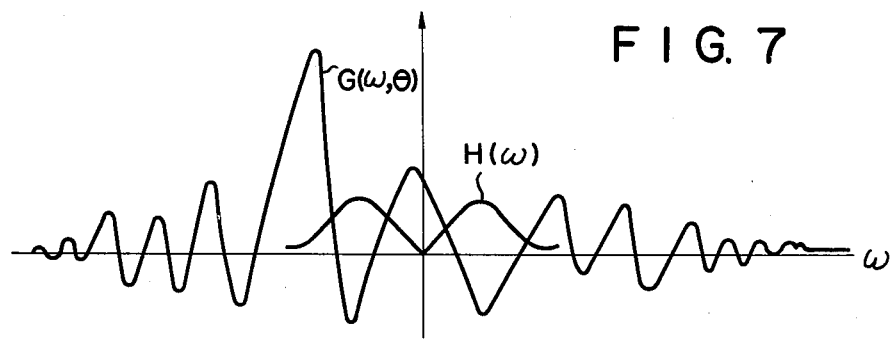
FIG. 7 is a graph showing by way of example the relative positions of the projection data and filter function in the frequency domain.

In FIG. 7 there are shown examples of the G(ω, θ) and H(ω) functions used in the equations (8) and (9). As seen from FIGS. 4 and 7, the H(ω) function converges with increasing absolute values of ω. At this time, therefore, the G(ω, θ)H(ω) also converges and the q(X, θ) function calculated using equation (8) converges to a value determined by X, θ and H(ω). It is understood from this that the q(X, θ) values may be calculated from equation (7) by using, in substitution for the value of G(ω, θ) calculated from the equation (9), the value of G'(ω, θ) calculated with the use of the following equation (10) obtained by charging the integral region of G(ω, θ) to an appropriately narrowed region $X_\alpha \sim X_\beta$. At this time, the integral region $X_\alpha \sim X_\beta$ can be selected such that the quality of the displayed image based on the value of q(X, θ) calculated from the equation (7) by using G'(ω, θ) is not deteriorated or degraded as compared with that of the displayed image obtained from the equation (8) by using G'(ω, θ)

$$G'(\omega,\theta) = \int_{X_\alpha}^{X_\beta} g(X,\theta)e^{-i\omega X}dX \quad (10)$$

The integral region $X_\alpha \sim X_\beta$ of the above equation (10) is determined in accordance with the foregoing consideration. By the use of equation (7) the value of g(X, θ) is determined with respect to each of numerous values of X included in the region $X_2 \sim X_3$ of FIG. 3.

Next, the value of θ is varied, whereby the value of the modified projection data q(X, θ) is determined with respect to each of numerous θ values applicable to the partial region 28. With respect to numerous points (x, y) included in the partial region 28, back projection based on the use of the equation (6) is carried out in accordance with the q(x, θ) values to permit reconstruction and display of the partial region 28. This is the same process of operation as in the above-described embodiment. The integral region $X_1 \sim X_4$ in FIG. 3 is substantially equivalent to the region which is substantially affected by the filter function H(ω) in corresponding relation to the integral region of the equation (10).

Also in this embodiment, the filtering operation is to be performed only with respect to a somewhat wider range corresponding to the partial region of the sectional portion so as to obtain the satisfactory effect of the filtering, and the operation for back projection is to be performed only for the partial region, so that the reconstruction and display of the image of the partial region may be achieved in a short time without reducing the image quality.

Figure 9:
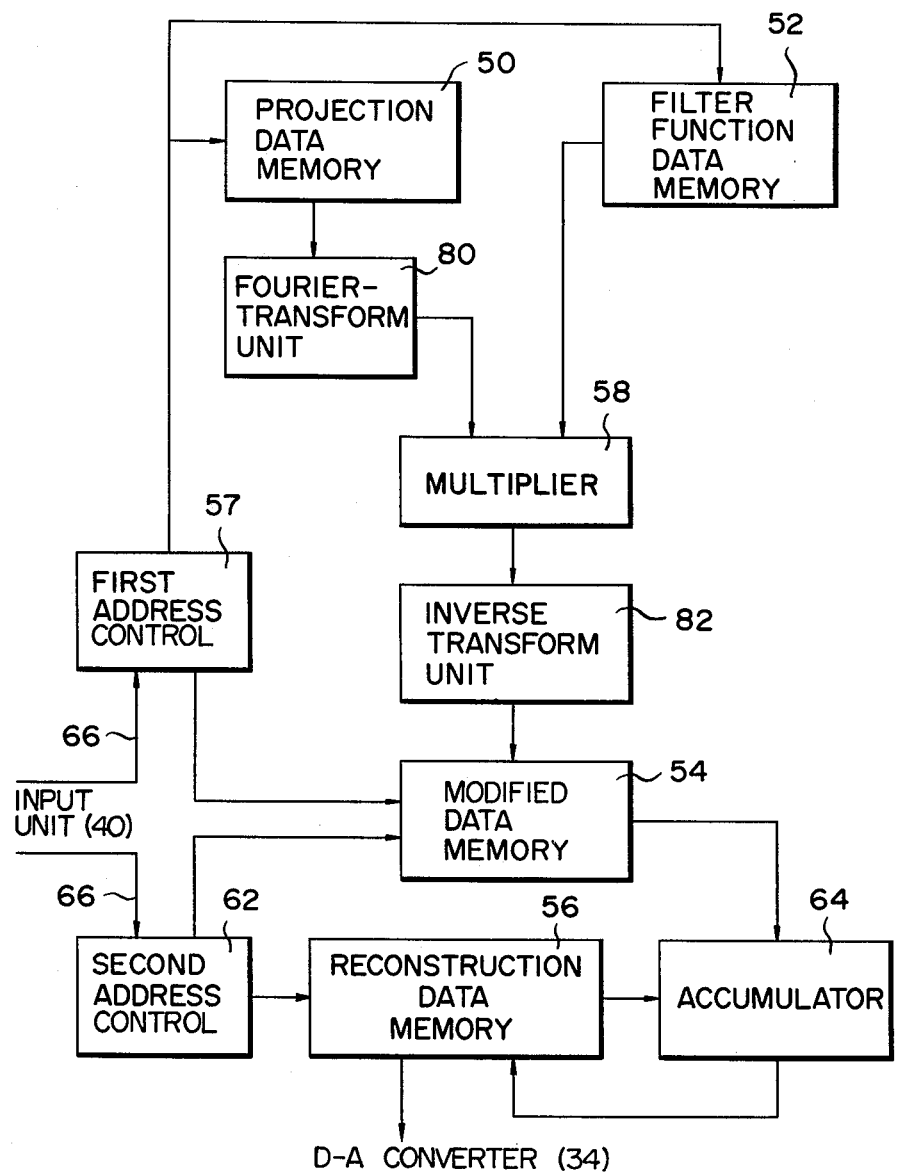
FIG. 9 is a block diagram showing a modified data calculating system and back projection system where a filtered-back projection computing method is employed for calculating the modified projection data.

Referring now to FIG. 9, there will be described the block diagram illustrating the reconstruction processing method used in this embodiment. In FIG. 9 the blocks in common with FIG. 8 are denoted by the same reference numerals. The projection data memory 50 stores the projection data values g(X,θ) collected for the different angles θ as the sampling data for the profiles 24. The filter function data memory 52 stores the sampling data of the filter function H(ω) subjected to Fourier transformation. The modified data memory 54 stores sets of modified projection data values q(X, θ) corresponding to various angles θ. Further, the reconstruction data memory 56 stores the absorption coefficients for the various pixels in the partial region of the sectional portion of the subject obtained from the back projection calculation. These memories 50, 52, 54 and 56 are included in the memory unit 22 of FIG. 1.

The first address control 57 designates the addresses of the projection data memory 50 and filter function data memory 52, reads out the data of the respectively designated memory addresses by means of a readout circuit (not shown), and supplies these data to the multiplier 58. Then the projection data read out from the memory 50 is Fourier transformed by a Fourier transform unit 80. The multiplier 58 multiplies the two supplied data values by each other, and delivers the product to an inverse transform unit 82. The inverse transform unit 82 inverse transforms the result produced by the multiplier 58, supplies the result to the modified data memory 54, which stores the calculation result of the inverse transform unit 82 in the address designated by the first address control 57. These operations are performed successively for all the angles θ used for the actual measurement of the projection data. Thus, the first address control 57, projection data memory 50, filter function data memory 52, Fourier transform unit 80, multiplier 58, inverse transform unit 82, and modified data memory 54 form the modified data calculating system which implements the procedures defined by equation (7).

The second address control 62 successively designates the addresses of the modified data memory 54, reads out data with respect to various values of X from a plurality of sets of modified projection data q(X, θ) corresponding to varied angles θ, and supplies the data to the accumulator 64. The accumulator 64 accumulates these data, and the results of such accumulation are stored in the address designated by the second address control 62 of the reconstruction data memory 56. Such operation is repeated for various values of X. The second address control 62, modified data memory 56, accumulator 64, and reconstruction data memory 56 form the back projection system to implement the operations defined by equation (6). The operations controlled by the first address control 57, Fourier transform unit 90, multiplier 58, inverse transform unit 82, second address control 62, and accumulator 64 shown in FIG. 9 may be performed by the CPU 26 of FIG. 1 under appropriate program control.

When the partial region 28 (FIG. 3) to be reproduced is designated by the input unit 40 of FIG. 1, the designating signal 66 (FIG. 8) is supplied to the first and second address controls 57 and 62. Then, the first address control 57 conducts address designation so as to read out the data from the projection data memory 50 and filter function data memory 52 only with respect to the ranges $X_1$ to $X_4$ of FIG. 3, thereby performing the operation for calculating the modified projection data (equation (8)) as already described. Receiving the partial region designating signal 66, the second address control 62 conducts address designation so as to read out the data from the modified data memory 54 only with respect to the range corresponding to the partial region or subsection 28 of FIG. 3, i.e. $X_2$ to $X_3$. The operation for back projection, in this case, is performed by accumulating the modified projection data values $q(X, \theta)$ at varied angles $\theta$ with respect to a number of points in the sectional portion to be reconstructed, the points being selected from within the range of the partial region 28 (FIG. 3).

According to the second embodiment which, unlike the first embodiment, employs the filtered-back projection method, the integral operation for obtaining the modified projection data is performed only with respect to the section corresponding to the partial region designated for display, plus the additional section provided for obtaining the satisfactory effect of filter functions, in the same manner as the first embodiment, and the back projection is conducted only with respect to the partial region. Consequently, the time required for reconstruction of the image of the portion to be displayed may usually be substantially reduced as compared with the conventional case where the region is not limited in such a manner. Notwithstanding the limited range of the projection data available for the above method of operation, the quality of the displayed image of the partial portion is not degraded.

Various modifications similar to those described in connection with the first embodiment may also be applied in the case of the second embodiment.

What we claim is:

1. In a system for image reconstruction by computed tomography wherein projection data signals are generated by detecting radiation beams projected through an internal area to be examined, said beams being projected in the plane of said area and at a plurality of scan angles relative thereto, said projection data signals representing the detected intensity of said beams, a method comprising the steps of:
   (a) storing said projection data signals;
   (b) storing a set of data values representing a filtering function;
   (c) reading from storage selected projection data signals generated by beams projected at a predetermined scan angle, said projection data signals being selected for readout under control of a designating signal defining a subsection area within said internal area to be examined such that only the projection data signals produced by beams passing through said subsection area and produced by beams passing through the regions immediately adjacent to and on either side of said subsection area are read out, said subsection area and said adjacent regions encompassing an area smaller than said internal area;
   (d) processing said signals read out from storage with said filtering function data values to produce a set of modified projection data signals;
   (e) storing said modified projection data signals;
   (f) repeating steps (c), (d) and (e) to generate and store additional modified projection data signals for beams projected at a plurality of different scan angles; and
   (b) accumulating in a memory pixel values representing the absorption coefficients for a plurality of points within said subsection area by reading from storage and back-projecting only those modified projection data signals corresponding to beams passing through said subsection area.

2. The method set forth in claim 1 wherein the width of said regions immediately adjacent to and on either side of said subsection area are determined by the spread of said filtering function.

3. The method set forth in claim 2 wherein said regions extend away from the edges of said subsection area by a distance necessary to encompass the projection data signals which, when convoluted with said filtering function, will materially modify projection data signals for beams within said subsection area.

4. The method set forth in claim 1 wherein step (d) includes the execution of mathematical operations for applying said filtering function data values to said projection data signals in real space.

5. The method set forth in claim 1 wherein step (d) includes the execution of mathematical operations for frequency domain multiplication of the Fourier transformation data values for said filtering function with the Fourier transformations of said projection data signals and for executing inverse Fourier transformation of the resulting data values to produce said modified data projection signals.

6. In a system for image reconstruction by computed tomography wherein projection data signala are generated by detecting radiation beams projected through an internal area to be examined, said beams being projected in the plane of said area and at a plurality of scan angles relative thereto, said projection data signals representing the detected intensity of said beams, the combination comprising:
   means for storing said projection data signals;
   means for storing a set of data values representing a filtering function;
   means sequentially operating to process said stored filtering function data values with a set of selected projection data signals stored for each of said plural scan angles, whereby a set of modified projection data signals is generated for each of said scan angles;
   said processing means including means for selecting for processing only those projection data signals in each scan angle set generated by beams passing through a predetermined subsection area within said internal area to be examined and by means passing through the regions immediately adjacent to and on either side of said subsection area, said subsection area and said adjacent regions encompassing an area smaller than said internal area;

means for storing said modified projection data signals; and means for converting said stored modified projection data signals into absorption coefficient values for a plurality of points within said subsection area by reading said modified projection data signals from storage and back-projecting only those signals corresponding to beams passing through said subsection area, whereby data is accumulated for reconstructing an image of said subsection area.

* * * * *

UNITED STATES PATENT OFFICE
CERTIFICATE OF CORRECTION

Patent No. 4,189,775　　　　　　　　　Dated February 19, 1980

Inventor(s) Tamon Inouye et al

It is certified that error appears in the above-identified patent and that said Letters Patent are hereby corrected as shown below:

IN THE ABSTRACT:

line 7,　　　　after "integration" insert --method--;

line 12,　　　delete "portion".

Signed and Sealed this

Fifth Day of August 1980

[SEAL]

Attest:

SIDNEY A. DIAMOND

Attesting Officer　　　Commissioner of Patents and Trademarks

UNITED STATES PATENT OFFICE
CERTIFICATE OF CORRECTION

Patent No. 4,189,775                    Dated February 19, 1980

Inventor(s) TAMON INOUYE ET AL

It is certified that error appears in the above-identified patent and that said Letters Patent are hereby corrected as shown below:

COLUMN 12,    line 51,    "signala" should be --signals--.

COLUMN 13,    line 3,     "means" should be --beams--.

Signed and Sealed this

Tenth Day of March 1981

[SEAL]

Attest:

RENE D. TEGTMEYER

Attesting Officer    Acting Commissioner of Patents and Trademarks